(12) United States Patent
Ogawa et al.

(10) Patent No.: US 6,306,409 B1
(45) Date of Patent: Oct. 23, 2001

(54) LIGHT-RESPONDING HIGH COLOR-RENDERING MAKEUP COSMETIC PREPARATION

(75) Inventors: Katsuki Ogawa; Daisuke Aso; Osamu Sakurai; Kazuhisa Ohno, all of Kanagawa (JP)

(73) Assignee: Shiseido Co., Ltd., Tokyo (JP)

( * ) Notice: Subject to any disclaimer, the term of this patent is extended or adjusted under 35 U.S.C. 154(b) by 0 days.

(21) Appl. No.: 09/431,096

(22) Filed: Nov. 1, 1999

(30) Foreign Application Priority Data

Nov. 2, 1998 (JP) .................................. 10-312308

(51) Int. Cl.$^7$ ................ A61K 6/00; A61K 7/00; A61K 7/021; A61K 7/025; A61K 7/035

(52) U.S. Cl. ................ 424/401; 424/63; 424/64; 424/69; 514/937

(58) Field of Search ................ 514/937, 844; 424/69, 64, 400, 63, 401

(56) References Cited

U.S. PATENT DOCUMENTS 5,690,916 * 11/1997 Kimura et al. .................... 424/59

FOREIGN PATENT DOCUMENTS

| 0 887 067 A2 | 12/1998 | (EP) . |
| 05051209 A | 3/1993 | (JP) . |
| 06345433 A | 12/1994 | (JP) . |
| 07258580 A | 10/1995 | (JP) . |
| 09165532 A | 6/1997 | (JP) . |
| 09165532 | * 6/1997 | (JP) . |

OTHER PUBLICATIONS

Database Chemical Abstracts Online, abstract 123:349 867, XP002129533—Japanese Patent No. 07 223816, Aug. 25, 1995.

Database Chemical Abstracts Online, abstract 124:126 209, XP002129554—Japanese Patent No. 07 258580, Oct. 09, 1995.

Database Chemical Abstracts Online, abstract 127:137 134, XP002129555—Japanese Patent No. 09 165532, Jun. 24, 1997.

Database Chemical Abstracts Online, abstract 128:326 276, XP002129556—A. Kimura, "Optical Property and Finishing Effect of New Materials for Makeup Foundations," *Zairyo Gijutsu*, 1998, vol. 16, No. 2, pp. 51–63. Japan.

* cited by examiner

*Primary Examiner*—Thurman K. Page
*Assistant Examiner*—S. Howard
(74) *Attorney, Agent, or Firm*—Snider & Associates; Ronald R. Snider

(57) ABSTRACT

In order to obtain a makeup cosmetic preparation having natural color-rendering property in response to intensity of surrounding light, a light-responding high color-rendering makeup cosmetic preparation of the present invention is characterized in that titanium oxide or titanium oxide compound, which has photochromic property to darken in response to intensity of irradiated ultraviolet ray, is coated on a surface of mica and metal or metal compound exists on a surface and/or inside of said photochromic titanium oxide coated mica and color of said metal or metal compound is observed as an object color, and wherein an observation color of said photochromic titanium oxide coated mica is changed by emphasizing an interference color generated by darkening of titanium oxide layer which is made of titanium oxide or titanium oxide compound in response to irradiation of ultraviolet ray, and wherein at least one of color tone in the cosmetic preparation is given by an observation color of the observation color changeable type photochromic titanium oxide coated mica.

9 Claims, 7 Drawing Sheets

The relation between reflectance of each wavelength and the amount of iron oxide which is added to titanium oxide coated mica The relation between the percentage of titanium oxide layer and photochromic property The relation between reflectance of each wavelength
and the amount of iron oxide which is added to titanium oxide coated mica The relation of the change of color-rendering property and the amount of the activating agent to be added The relation between color-rendering property and returning property, which is calcinated at each temperature The reflectance of each wavelength in reflected interference light which is shown by the photochromic titanium oxide coated mica calcinated at each temperature The relation of the properties of reflectance
concerning titanium oxide coated mica in each wavelength The relation of reflectance in each wavelength in the reflected light of the powdery foundation of the present invention

LIGHT-RESPONDING HIGH COLOR-RENDERING MAKEUP COSMETIC PREPARATION

RELATED APPLICATIONS

This application claims the priority of Japanese Patent Application No. 10-312308 filed on Nov. 2, 1998, which is incorporated herein by reference.

FIELD OF THE INVENTION

The present invention relates to a makeup cosmetic preparation having photochromic property and, in particular, to an improvement of a makeup cosmetic preparation which changes its color to natural observation color in response to intensity of surrounding light.

BACKGROUND OF THE INVENTION

"Aesthetic function" to show more beautifully, "sensuous function" to give comfortableness, "functionality" such as cosmetic durability and prevention of secondary adhesion, and so on are listed as basic function required to the makeup cosmetic preparation.

The feel of material in case of applying the makeup cosmetic preparation to the face has been generally adjusted by compounding various glossy pigments such as the titanium oxide coated mica pigments in order to achieve aesthetic function. Such titanium oxide coated mica pigments that titanium dioxide layer is formed on the surface of fine flaky mica, have iridescent luster and various interference colors, as described in Cosmetic Ingredients Standard. It is generally manufactured by hydrolyzing inorganic salt solution of titanium such as titanyl sulfate, depositing hydrous titanium dioxide on the surface of mica, and heating it. The interference colors of thus generated titanium oxide coated mica pigments show various colors in accordance with thickness of titanium dioxide coated layer on the surface of mica. However, any object colors thereof are nearly white.

Thereupon, some methods for giving various object colors in the titanium oxide coated mica pigments have been considered. The most general method is to add coloring pigments such as iron oxide, ultramarine blue, chromium oxide, carbon black and carmine on the surface of the generated titanium oxide coated mica pigments. However, this method is defective in decreasing transparency of titanium oxide coated mica. As compared with this, the colored titanium oxide coated mica pigments, which does not spoil transparency of titanium oxide coated mica by doping various metals or metal compounds on mica in titanium oxide coated mica, have been developed.

On the contrary, various functions are recently required to the pigments. As one of such pigments, the pigments having the so-called photochromic property (or phototropic property) are beginning to attract. As the products applying photochromic property, light-modulating glass and color-changeable makeup cosmetic preparation have been developed.

Only single interference color, however, is obtained in the conventional titanium oxide coated mica pigments. Also, when the titanium oxide coated mica pigments are compounded to a foundation, it become nearly white as a whole under sunlight where intensity of light is strong, while it become dark with yellow as a whole in the room where intensity of light is weak. Therefore, it is highly desired to develop the pigment, which has natural color-rendering property in response to intensity of light. The present inventors have studied diligently in order to meet these expectations. Color tones of titanium oxide which is comprised in titanium oxide coated mica are changed in response to intensity of light by giving photochromic property to titanium oxide in titanium oxide coated mica. The present inventors have found that this working emphasizes the interference color that is generated on titanium oxide coated mica and the pigments can function as extremely useful pearl pigment whose observation color is changeable. Thus, the present inventors have developed the titanium oxide coated mica pigment that the observation color changes in response to light and have suggested the pigment in Unexamined Japanese Patent Publication No. Hei 9-165532.

Cosmetic preparations having light-responding color-rendering effect, which respond to intensity of surrounding light have not been developed yet.

SUMMARY OF THE INVENTION

In view of the foregoing problem in the prior art, an object of the present invention is to provide a makeup cosmetic preparation having natural color-rendering property in response to intensity of surrounding light.

A light-responding high color-rendering makeup cosmetic preparation in accordance with the present invention for attaining the above-mentioned objects, is a makeup cosmetic preparation comprising a photochromic titanium oxide coated mica, wherein said photochromic titanium oxide coated mica is an observation color changeable type photochromic titanium oxide coated mica wherein titanium oxide or titanium oxide compound, which has photochromic property to darken in response to intensity of irradiated ultraviolet ray, is coated on a surface of mica and wherein metal or metal compound exists on a surface and/or inside of said photochromic titanium oxide coated mica and color of said metal or metal compound is observed as an object color and wherein an observation color of said photochromic titanium oxide coated mica is changed by emphasizing an interference color generated by darkening of titanium oxide layer, which is made of titanium oxide or titanium oxide compound in response to irradiation of ultraviolet ray, and wherein at least one of color tone in the cosmetic preparation is given by an observation color of said observation color changeable type photochromic titanium oxide coated mica.

In the present invention, it is preferable that layer thickness of titanium oxide layer, which is comprised in the titanium oxide coated mica in said observation color changeable type photochromic titanium oxide coated mica, is adjusted in order that color tone of the interference color that is generated by titanium oxide layer may shows different color with the object color.

It is also preferable that layer thickness of titanium oxide layer, which is compounded in titanium oxide coated mica of said observation color changeable type photochromic titanium oxide coated mica, is adjusted in order that color tone of the interference color that is generated by titanium oxide layer may shows a complementary color or color gamut in the vicinity of the complementary color of the object color.

It is also preferable that said observation color changeable type photochromic titanium oxide coated mica is a photochromic titanium oxide coated mica that reflectance of the light around long wavelength range of visible rays decreases in a light place and increases in a dark place.

It is also preferable that said observation color changeable type photochromic titanium oxide coated mica comprises iron oxide or a compound which is mainly composed of iron oxide.

It is also preferable that a percentage of titanium oxide which is compounded in titanium oxide coated mica of said observation color changeable type photochromic titanium oxide coated mica is 47 to 57%.

It is also preferable that said observation color changeable type photochromic titanium oxide coated mica is calcinated at 850 to 950° C.

It is also preferable that an amount of said observation color changeable type photochromic titanium oxide coated mica is 0.1 to 30 wt %.

It is also preferable that 1 to 30 wt % of a photochromic titanium oxide, which only changes the object color or lightness with light, is compounded in the makeup cosmetic preparation together with said observation color changeable type photochromic titanium oxide coated mica.

BEST MODE FOR CARRYING OUT THE INVENTION

Figure 1:
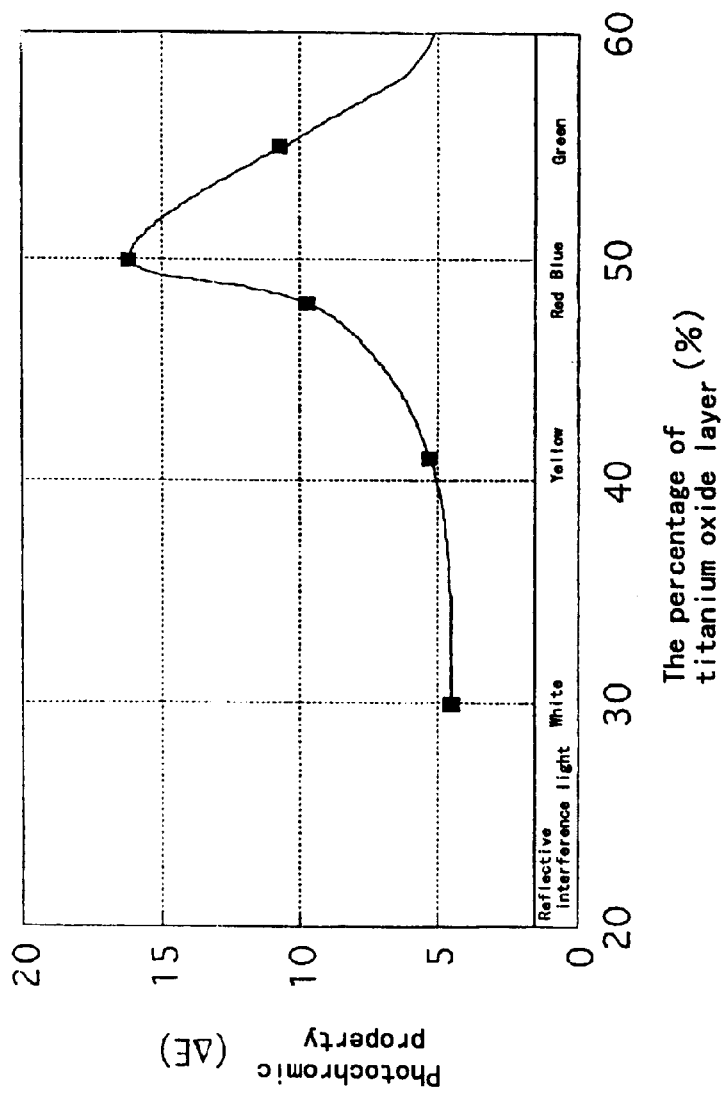
FIG. 1 is a graphic chart showing the relation between the percentage and photochromic property of titanium oxide layer.

The present invention is an observation color changeable type photochromic titanium oxide coated mica wherein titanium oxide or titanium oxide compound, which has photochromic property to darken in response to intensity of irradiated ultraviolet ray, is coated on a surface of mica and wherein metal or metal compound exists on a surface and/or inside of said photochromic titanium oxide coated mica and color of said metal or metal compound is observed as an object color and an observation color of said photochromic titanium oxide coated mica is changed by emphasizing an interference color generated by darkening of titanium oxide layer, which is made of titanium oxide or titanium oxide compound in response to irradiation of ultraviolet ray, and wherein at least one of color tone in the cosmetic preparation is given by the observation color of said observation color changeable type photochromic titanium oxide coated mica.

"At least one of color tone in the cosmetic preparation" mentioned hereinbefore means a color element for the purpose of composing color tone of the cosmetic preparation when the color tone of some cosmetic preparation is composed of various pigments having different color tone each other.

For explaining an observation color changeable type photochromic titanium oxide coated mica which is used for the present invention, the three words is used, it are "an observation color" "an interference color" and "an object color". "an observation color" means the color tone of the photochromic titanium oxide coated mica that is actually observed by visual observation. "an interference color" means the color tone of interference light that arise at titanium or titanium oxide compound which is coated on a surface of mica. "an object color" means the color tone of the photochromic titanium oxide coated mica that is observed by visual observation when interference light do not arise at the photochromic titanium oxide coated mica.

Lightness of the observation color changeable type photochromic titanium oxide coated mica changes with photochromic property of titanium oxide layer in response to intensity of surrounding ultraviolet ray. The interference color generated in titanium oxide coated mica is emphasized therewith. Accordingly, lightness and hue of the observation color of the photochromic titanium oxide coated mica change at the same time, e.g., the mixed color tone of interference light and the object color of titanium oxide coated mica is shown in a light place and color tone of object color is mainly shown in a dark place.

The observation color of the photochromic titanium oxide coated mica mentioned in this specification means the color tone of the photochromic titanium oxide coated mica that is actually observed by visual observation, from the elements such as object color and interference color.

The present inventors diligently and repeatedly studied in order to obtain the cosmetic preparation which has natural color-rendering property matching with the condition of surrounding light in the case where said observation color changeable type photochromic titanium oxide coated mica pigment is compounded in the cosmetic preparation and accordingly, accomplished the present invention.

In time of explaining the present invention, color tone, complementary color and photochromic property are defined as follows.

Definition of Color Tone

To sense a color means abstraction of only a sense such as red, yellow, green blue and etc., which have no specific meaning, from perception. Namely, it means perceptual phenomenon that corresponds to color stimulus with one on one. Accordingly, it is most preferable to show color sensation with Munsell color system. In order to be equal rate sensuously, Munsell color system defines hue, lightness and chroma to the directions of θ, z and r of cylindrical coordinates of three-dimensional space, respectively, in accordance with three attributes of color. In Japan, JIS (JIS Z 8721) adopted this color system in 1958 as a method of presentation by three attributes of color. In Munsell color system, there are 10 basic hues and examples of them include Red (R), Yellow (Y), Green (G), Blue (B), Purple (P), Yellowish Red (YR), Green Yellow (GY), Blue Green (BG), Purple Blue (PB) and Red Purple (PR). As a result of colorimetry and conversion with Munsell color system, most of the color in each area (hue) can be defined as the color therein.

Definition of Complementary Color

Complementary color signifies the relation that a mixed color becomes achromatic color in the case where two colors are added and mixed in a certain rate. Namely, two colors to be mixed are complementary color when the mixed color of two colors becomes white light in colored light and becomes glay in object color. Examples of color relation, which becomes complementary color, include red and green, blue and orange, yellow and purple and so on.

Definition of Photochromic Property

In the present invention, photochromic property was studied as follows.

A sample that 5 g of powder in 2.8 by 4.5 cm angular medium plate was molded by the pressure under 30 kg/cm$^2$, was used.

As the condition of light, UV-A fluorescent light (FL20SBLB manufactured by TOSHIBA) and UV-B fluorescent light (FL20S·E manufactured by TOSHIBA) are fixed at intervals of 15 cm, respectively. Heights of them are adjusted in order that intensity of ultraviolet ray may become 2 mW/cm$^2$ by an ultraviolet ray intensity meter (SUV-T type manufactured by TORAY).

In actual measurement,
(1) The sample left for 10 hours at room temperature in a dark place was measured by a colorimeter (CM-1000RH manufactured by MINOLTA).
(2) The color that the sample was darkened by irradiating said ultraviolet ray for 30 minutes was measured in the same manner.
(3) The color that the irradiated sample was left for 3 hours at room temperature in a dark place was measured in the same manner.
Photochromic property is
$7 \leq A \leq 20$ and
$B \leq 5$,
when color difference $\Delta E$ of (1) and (2) is defined as A and, color difference $\Delta E$ of (1) and (3) is defined as B.

In case of satisfying such conditions, lightness is changed by photochromic property when $\Delta E$ is less than 10, as change of color tone by intensity of light. And it is possible to see the change of hue along with lightness by photochromic property when $\Delta E$ is 10 or more. Consequently, 10 or more of $\Delta E$ means high color-rendering property.

In this specification, the photochromic titanium oxide coated mica means the observation color changeable type photochromic titanium oxide coated mica by irradiation of light without otherwise stated. Also, the conventional photochromic titanium oxide means the photochromic titanium oxide that color tone of the observation color seldom change by irradiation of light and lightness changes mainly.

In here, methods for manufacturing observation color changeable type photochromic titanium oxide coated mica pigment that is used preferably in the present invention will be explained.

Manufacturing Method of Observation Color Changeable TypePhotochromic Titanium Oxide Coated Mica Pigment As the method for obtaining the observation color changeable type photochromic titanium oxide coated mica pigment, mica, titanium oxide and one or more of metal or metal compound comprising metal or metal compound, which may be a photochromic property activating agent, exist together. These metals are calcinated in the condition of coexistence.

In here, it is preferable that an amount of the photochromic property activating agent is 0.1 to 10% and calcination temperature is 750 to 950° C.

As such manufacturing method, it is possible to give photochromic property to titanium oxide, and to combine mica, titanium oxide and at least one of metal or metal compound.

It is preferable that mica and titanium oxide are in the state of titanium oxide coated mica, which forms titanium oxide layer on mica layer.

In the manufactured observation color changeable type photochromic titanium oxide coated mica, the object color of the pigment is given by the metal or metal compound, which exists on the surface and/or inside of titanium oxide coated mica. Namely, when iron or iron compound, cobalt or cobalt compound, nickel or nickel compound and copper or copper compound exists on the surface and/or inside of titanium oxide coated mica, the object color becomes yellowish orange, purple, yellow green and reddish brown, respectively.

Examples of the metal which are generally used to give photochromic property in titanium oxide include iron, chromium, copper, nickel, manganese, cobalt and molybdenum and metal powder itself or salts thereof such as sulfate, chloride, nitrate and acetate, oxide thereof and hydrate thereof.

The object color of the observation color changeable type photochromic titanium oxide coated mica pigment is also given by these metals or salts thereof, oxide thereof and chloride thereof those are used as the photochromic property activating agent. Therefore, it is not always used no matter what kind of activating agents. It is preferable to select the activating agent according to the color to be applied to the pigment. For example, red iron oxide, yellow iron oxide and black iron oxide are selected in the case where object color of yellowish orange is required.

It is possible to manufacture the observation color changeable type photochromic titanium oxide coated mica that is used preferably in the present invention by satisfying the required conditions mentioned hereinbefore. Color tone of observation color in the manufactured observation color changeable type photochromic titanium oxide coated mica pigment changes by irradiation of light, and in particular, ultraviolet ray.

In addition to said photochromic titanium oxide coated mica, water, powders, oils, surfactants, lower alcohols, polyhydroxy alcohols, humectants, antiseptics, polymers, antioxidants, ultraviolet absorbents, fragrance, various drags and the like may be compounded in the makeup cosmetic preparation of the present invention within the qualitative and quantitative range that color-rendering property in response to the light condition of the present invention is not spoiled.

Powder ingredients, which may be compounded in the makeup cosmetic preparation of the present invention, the powders that are generally used in the cosmetic preparation, can be listed. Examples of the powder include: inorganic powders such as talc, kaolin, mica, sericite, muscovite mica, biotite, phlogopite, synthetic mica, vermiculite, magnesium carbonate, calcium carbonate, aluminum silicate, barium silicate, calcium silicate, magnesium silicate, metal tungstate, magnesium, silica, zeolite, barium sulfate, calcined calcium sulfate, calcined gypsum, calcium phosphate, fluorine apatite, hydroxy apatite, ceramic powder, metallic soap (zinc myristate, calcium palmitate, and aluminum stearate); organic powders such as polyamide resin powder, polyethylene powder, methyl polymethacrylate powder, polystyrene powder, copolymer powder of styrene and acrylic acid, benzoguanamine resin powder, polyethylene tetrafluoride powder, and cellulose powder; inorganic white pigments such as titanium dioxide and zinc oxide; inorganic red pigments such as iron oxide (red iron oxide) and iron titanate; inorganic brown pigments such as γ-iron oxide; inorganic yellow pigments such as yellow iron oxide and ocher; inorganic black pigments such as black iron oxide, carbon black, and low-order titanium oxide; inorganic violet pigments such as mango violet and cobalt violet; inorganic green pigments such as chromium oxide, chromium hydroxide, and cobalt titanate; inorganic blue pigments such as ultramarine blue and iron blue; pearl pigments such as titanium oxide coated mica, titanium oxide coated bismuth oxychloride, titanium oxide coated talc, color titanium oxide coated mica, bismuth oxychloride and fish scale flake; metal powder pigments such as aluminum powder and copper powder; organic pigments such as Red No.202, Red No.205, Red No.220, Red No.228, Red No.405, Orange No.203, Orange No.204, Yellow No.205, Yellow No.401, and Blue No.404; organic pigments based on lakes of zirconium, barium and aluminum or the like such as Red No.3, Red No.104, Red No.227, Red No.401, Orange No.205, Yellow No.4, Yellow No.202, Green No.3 and Blue No.1; and natural coloring matters such as chlorophyll and β-carotene Oils, which may be compounded in the makeup cosmetic preparation of the present invention, oils that are generally used in the cosmetic preparation, can be listed. Examples of oils include: liquid fats and oils such as avocado oil, camellia oil, macadamia nut oil, mink oil, olive oil, castor oil, jojoba oil, triglycerol and glyceryl trioctanoate; solid fats and oils such as coconut oil, hydrogenated coconut oil, palm oil, beef tallow, mutton tallow, Japanese wax and hydrogenated castor oil; wax such as beeswax, candelilla wax, carnauba wax, Chinese wax, spermaceti, lanolin and lanolin hydrogenated; hydrocarbons such as liquid paraffin, squalane, paraffin, ceresine, petrolatum, squalene and mycrocrystalline wax; higher fatty acids such as lauric acid, myristic acid, palmitic acid, stearic acid, behenic acid, oleic acid, 12-hydroxystearic acid, isostearic acid, linoleic acid and linolenic acid; higher alcohols such as lauryl alcohol, cetyl alcohol, stearyl alcohol, behenyl alcohol, oleyl alcohol, monostearyl glyceryl ether, monopalmityl glyceryl ether, cholesterol, phytosterol and isostearyl alcohol; ester oils such as isopropyl myristate, cetyl octanoate, 2-octyldodecyl myristate, butyl stearate, decyl oleate, ethylene glycol dioctanoate, diisostearyl malate, trimethylolpropane trioctanoate, trimethylolpropane triisostearate, pentaerithrityl tetraoctanoate, glyceryl trioctanoate, glyceryl triisostearate, ethyl acetate, butyl acetate and amyl acetate; and silicones such as dimethylpolysiloxane, methylphenyl polysiloxane, methyl hydrogen polysiloxane, decamethylcyclopentasiloxane, octamethylcyclotetrasiloxane, silicon resins forming three-dimensional network and silicone rubber. Oils are not limited to the above ingredients. Oils may be optionally used with one or more in the makeup cosmetic preparation of the present invention.

In the makeup cosmetic preparation of the present invention, surfactants that are generally compounded in the cosmetic preparations may be used regardless of its ionicity. Examples of anionic surfactants include: fatty acid soaps such as soap base and sodium laurate; higher alkylsulfate such as sodium lauryl sulfate; alkyl ether sulfate such as triethanolamine polyoxyethylene (shortened "POE" in the following) laurylether sulfate; N-acyl sarcosinate such as sodium N-lauroyl sarcosinate; higher fatty acid amidosulfonate such as sodium-N-cocoyl N-methyl taurate; phosphate esters such as POE stearylether phosphate; sulfosuccinate such as di-2-sodium ethylhexyl sulfosuccinate; alkylbenzene sulfonate such as sodium dodecylbenzenesulfonate; N-acyl-L-glutamates such as disodium N-stearoyl-L-glutamate; higher fatty acid ester sulfates such as sodium hydrogenated glyceryl cocoate sulfate; sulfating salts such as turkey red oil; POE alkyl ether carbonate, POE alkyl aryl ether carbonate, α-olefin sulfonate, higher fatty acid ester sulfonate, secondary alcohol sulfate, higher fatty acid alkylol amide sulfate, sodium lauroyl monoethanol amide succinate, ditriethanol-amine N-palmitoylaspartate and sodium caseinate.

Examples of cationic surfactants include: alkyltrimethylammonium salts such as stearyl trimethylammonium chloride; dialkyldimethylammonium salts such as distearyl-dimethylammnium chloride; alkyl pyridinium salts such as cetylpyridinium chloride; alkyl quaternary ammonium salts, aLkyldimethylbenzylammonium salts, alkylisoquinolinium salts, dialkylmorpholinium salts, POE alkylamine, alkylamine salts, polyamine fatty acid derivatives, amyl alcohol fatty acid derivatives, benzalkonium chloride and benzethonium chloride.

Examples of ampholytic surfactants include: imidazolinium ampholytic surfactants such as sodium 2-undecyl-N, N,N-(hydroxyethylcarboxymethyl)-2-imidazolinium and betaine ampholytic surfactants such as lauryl dimethylaminoacetic acid betaine.

Examples of lipophilic nonionic surfactants include: sorbitan fatty acid esters such as sorbitan monoisostearate and sorbitan sesquioleate; glycerin polyglycerin fatty acids such as glyceryl monostearate; propylene glycol fatty acid esters such as propylene glycol monostearate; hydrogenated castor oil derivatives and glyceryl alkyl ether.

Examples of hydrophilic nonionic surfactants include: POE sorbitan fatty acid esters such as POE sorbitan monostearate; POE sorbitol fatty acid esters such as POE sorbitol monooleate; POE glyceryl fatty acid esters such as POE glyceryl monoisostearate, POE alkyl ethers such as POE stearyl ether and POE cholesteryl ether; POE alkylphenyl ethers such as POE nonylphenyl ether; pluaronics such as Pluronic; POE·polyoxypropylene (shortened as POP in the following) alkyl ethers such as POE·POP cetyl ether; tetra POE·tetra POP ethylenediamine condensations such as Tetronic; POE hydrogenated castor oil derivatives such as POE castor oil and POE hydrogenated caster oil; POE beeswax·lanolin derivatives, alkanolamide, POE propylene glycol fatty acid ester, POE alkylamine, POE fatty acid amide, sucrose fatty acid ester, POE nonylphenyl formaldehyde condensation, alkylethoxydimethylamine oxide and trioleyl phosphate.

The present invention is not restricted to the surfactants mentioned hereinbefore. It is possible to compound one or more of these surfactants optionally in the makeup cosmetic preparation of the present invention.

Available form of makeup cosmetic preparation in the present invention is not particularly restricted and various forms can be adopted according to each purpose. For example, make-up base, foundation, face powder, cheek powder, lipstick, mascara, eye shadow, eye liner and the like can be adopted.

The preferred embodiments of the present invention are explained in detail as follows.

The light-responding high color-rendering makeup cosmetic preparation of the present invention shows useful light-responding property by the photochromic titanium oxide coated mica to be compounded. Accordingly, it is important to study the properties of the pigment to be compounded.

Study in Layer Thickness of Titanium Oxide Layer

The interference color produced by titanium oxide coated mica is determined by thickness of titanium oxide layer, which is laminated on mica. For example, in the case where the ratio of titanium oxide layer with respect to mica whose average particle diameter is 20 μm and which becomes a nucleus of titanium oxide coated mica, is about 30%, about 40%, about 47%, about 50% and about 55%, the interference color becomes white, yellow, red, blue and green, respectively.

Mixing 1 wt % of iron oxide with titanium oxide coated mica that titanium oxide layer is coated on mica having 20 μm of average particle diameter in several ratios and calcinating the mixture at 900° C., thereby yielding the pigment having reddish orange object color. The pigment was used as a sample and influence on photochromic property due to the ratio of titanium oxide layer of said titanium oxide coated mica was studied.

The relation between the ratio of titanium oxide layer of said titanium oxide coated mica and photochromic property is shown in FIG. 1 under the definition of photochromic property mentioned hereinbefore.

As is clearly shown in FIG. 1, it was not observed satisfactory photochromic property in the case where the ratio of titanium oxide layer was 45%. Photochromic property was low in the case where the ratio of titanium oxide layer was 60%. High photochromic property was shown in the case where the ratio of titanium oxide layer was about 50%. In this ratio of titanium oxide layer, the color of interference light becomes blue to red purple to red and nearly complementary color with the object color of the pigment.

The reflected light mixing a transmitted interference light and a reflected interference light at titanium oxide layer becomes white in the case where ultraviolet ray is not irradiated in the observation color changeable type photochromic titanium oxide coated mica pigment having about 50% of titanium oxide layer used in this test. The reflected light on the surface of mica also becomes white. The interference light that is produced between the reflected light on the surfaces of titanium oxide coated mica and titanium oxide becomes white in the composition of titanium oxide coated mica used in this test. And, the color of this pigment becomes bright reddish orange because the metals such as iron oxide, which have the reflected light of reddish brown on the surface of titanium oxide are combined in this pigment.

The reflected light on the surface of mica is white in case of irradiating ultraviolet ray on this pigment. However, only the reflected interference light is produced because photochromic property is given in titanium oxide layer. Namely, the transmitted interference light was absorbed into titanium oxide layer since color tone of titanium oxide layer changes to gray or black.

Accordingly, the interference light that is produced between the reflected light on the surfaces of titanium oxide coated mica and titanium oxide becomes blue to red in said pigment. A whole of pigment shows dark or blackish red purple to blue together with reddish orange, which is the reflected light of iron oxide.

Consequently, hue and lightness change in response to intensity of light in this pigment. The pigment shows bright reddish orange in the place where intensity of light is weak, while it shows dark or blackish red purple to blue in the place where intensity of light is strong.

Therefore, in order to direct high color-rendering property by compounding these pigments in the makeup cosmetic preparation, it is proper that: the object color of titanium oxide coated mica is adjusted to the color tone to be given in cosmetic preparation and; the ratio of titanium oxide layer is adjusted in order that the color tone produced in titanium oxide coated mica becomes complementary color of the object color or the vicinity thereof.

However, it is not necessary to adjust color tone to complementary color of the object color or the vicinity thereof, because photochromic property, which satisfies the above-mentioned definition of photochromic property, is obtained. The difference of interference light that is occurred by the ratio of titanium oxide layer can be determined voluntarily with the consideration of color tone which changes in response to light.

However, the interference color shows extremely low photochromic property and the above-mentioned definition of photochromic property is not satisfied in the case where the ratio of titanium oxide layer is determined to produce the interference light of the color tone which is similar to the object color. In the titanium oxide coated mica use in this test, the ratio of titanium oxide layer, which is less than 45%, corresponds to such color tone. Its photochromic property shows nothing but $\Delta E \approx 5$ and only lightness is changed. Accordingly, the ratio of titanium oxide layer producing the interference color which is similar to the object color of photochromic titanium oxide coated mica.

Study in Amount of Photochromic Property Activating Agent

It is found that the color tone which is intended to give cosmetic preparation is mainly given by the object color of titanium oxide coated mica as shown in the test hereinbefore. An observation color changeable type photochromic titanium oxide coated mica was prepared according to the above-mentioned method, i.e., by using iron oxide as the photochromic property activating agent, adjusting the ratio of mica:titanium oxide to 51:49 to 57:43 and calcinating the mixture at 900° C. The color of thus obtained titanium oxide coated mica whose object color was reddish orange and whose interference color was blue, was tested with changing the amount of iron oxide, which was the activating agent to be added to titanium oxide coated mica. The amount of iron oxide added to titanium oxide coated mica was changed within the range between 0.1 to 10 wt % that the observation color changeable type photochromic titanium oxide coated mica showed favorable photochromic property. This result is shown in FIG. 2.

Figure 2:
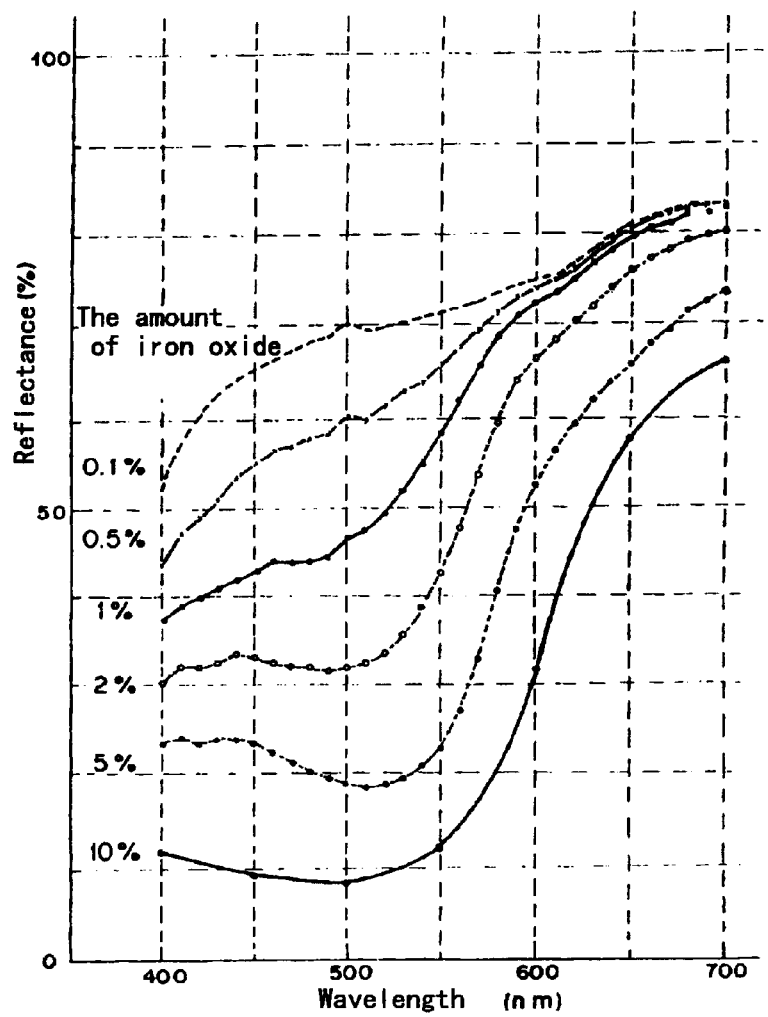
FIG. 2 is a graphic chart showing the amount of iron oxide which is added to titanium oxide coated mica and reflectance of each wavelength in reflected interference light which is shown by the photochromic titanium oxide coated mica.

It is understood that reflectance in each wave length of light is changed according to the amount of iron oxide as shown in FIG. 2. The color of titanium oxide coated mica used in this test is reddish orange. Accordingly, the color tone is evaluated on the premise to manufacture a fresh-colored makeup cosmetic preparation, which matches color of bare skin. The cosmetic preparation that is added about 1 wt % of iron oxide is favorable with respect to the color tone since the color tone of such cosmetic preparation is similar to the one of bare skin.

Measurement of spectral reflectance in this specification is measured by irradiating white light into the measuring object and by separating the reflected light from the measuring object.

Photochromic property of titanium oxide coated mica changes according to the amount of the photochromic property activating agent. This change was tested by using the above-mentioned sample. This result is shown in FIG. 3.

Figure 3:
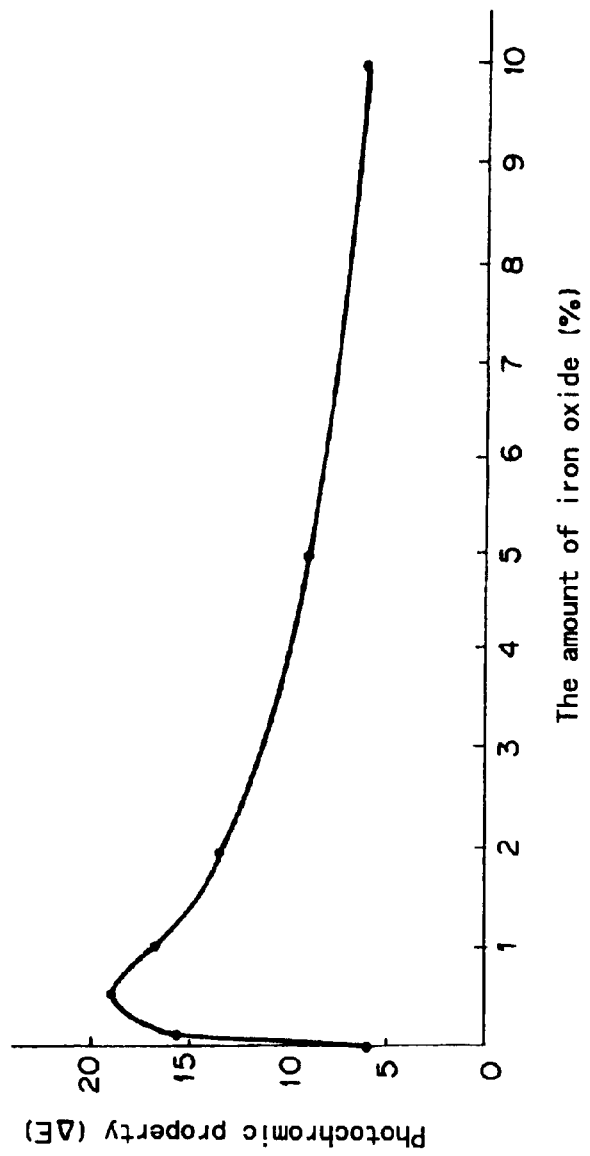
FIG. 3 is a graphic chart showing the relation of the change of color-rendering property, which is shown by titanium oxide coated mica according to the amount of the activating agent to be added.

It is understood that photochromic property changes largely according to the amount of iron oxide as shown in FIG. 3. Therefore, it is observed that the cosmetic preparation which is added 0.1 to 2.5 wt % of iron oxide shows favorable photochromic property in the case where the pigment is compounded in a fresh-colored makeup cosmetic preparation such as a foundation. In particular, the cosmetic preparation which is added 0.1 to 1.5 wt % of iron oxide shows high photochromic property.

In consideration of the result obtained from FIGS. 2 and 3, it is preferable that the amount of iron oxide is 0.3 to 2.0 wt %, and more particular, 0.4 to 1.5 wt % in order to obtain a fresh-colored makeup cosmetic preparation having high photochromic property matching with bare skin by adding iron oxide, which is a photochromic property activating agent, to titanium oxide coated mica.

Study in Calcination Temperature

Photochromic base glossy pigment was prepared according to the above-mentioned method, i.e., by using 1 wt % of iron oxide as a photochromic property activating agent and titanium oxide coated mica whose ratio of titanium oxide layer was 50% and whose interference color was blue. Color-rendering property and influence on the color tone of the interference light produced in titanium oxide coated mica were tested with changing calcination temperature. Calcination temperature was changed within the range of 500 to 1000° C. These results are shown in FIGS. 4 and 5.

Figure 4:
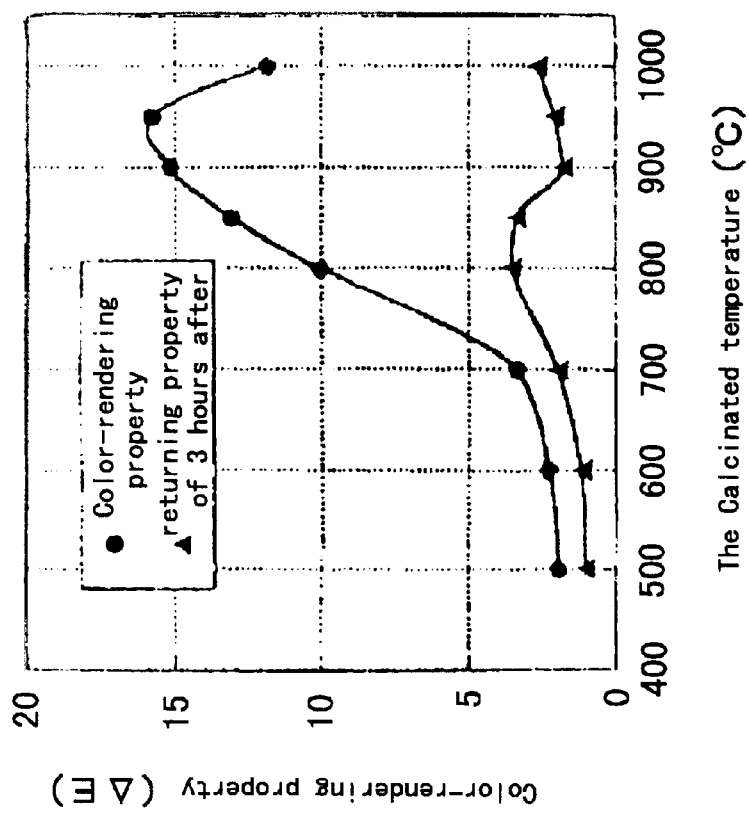
FIG. 4 is a graphic chart showing the relation between color-rendering property and returning property of the photochromic titanium oxide coated mica, which is calcinated at each temperature.

FIG. 4 shows color-rendering property and returning property of the photochromic titanium oxide coated mica, which is calcinated at each temperature. As shown in FIG. 4, color-rendering property gradually increases in the case where calcination temperature is over 700° C. The highest color-rendering property can be obtained at 950° C. However, it is understood that titanium oxide coated mica, which is calcinated at 900° C. shows the largest change of the color tone in light and dark places in consideration of returning property that the color tone returns while leaving the pigment in a dark place.

Figure 5:
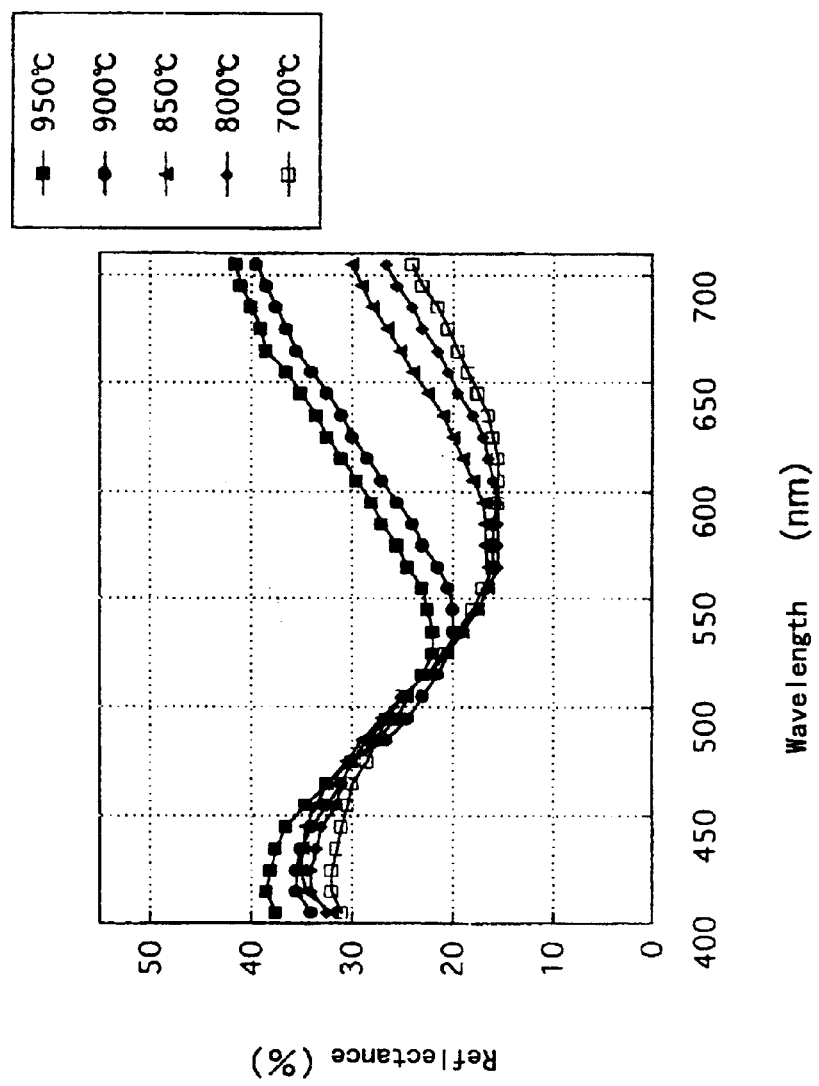
FIG. 5 is a graphic chart showing reflectance of each wavelength in reflected interference light which is shown by the photochromic titanium oxide coated mica calcinated at each temperature.

FIG. 5 shows the reflectance of each wave length in reflected interference light which was made by the photochromic titanium oxide coated mica calcinated at each temperature. In here, photochromic titanium oxide coated mica was applied on aketo paper of black substrate. As shown in FIG. 5, reflectance of reflected interference light increases with rising of calcination temperature. In particular, reflectance of reflected interference light having wave length more than 550 nm increases drastically in the case where calcination temperature is over 850° C. It is seemed that the reason for changing blue to red in reflected interference light is because a combined body with iron oxide is favorably formed on the surface of titanium oxide coated mica in the case where calcination temperature is 850° C. or more.

From the result of FIG. 5, it may be estimated that lightness of photochromic titanium oxide coated mica calcinated at 850° C. or more increases and reddish orange is shown under fluorescent light of indoor. Also, it also may be estimated that lightness of titanium oxide coated layer decreases and the observed color tone favorably changes to red purple with red nearly blue by photochromic property under sunlight.

Judging from the result of the tests concerning color-rendering property and returning property of FIG. 4, it is preferable that calcination temperature is 850 to 950° C. in order to obtain the makeup cosmetic preparation having high color-rendering property in response to surrounding light condition.

In considering the viewpoint hereinbefore, the pigment that 0.3 to 2.0 wt % of the photochromic property activating agent is added to titanium oxide coated mica whose ratio of titanium oxide layer is 47 to 57% and calcination temperature is 850 to 950° C., seems to be effective.

Study in Responding Property with Respect to Surrounding Light Condition of Titanium Oxide Coated Mica An observation color changeable type photochromic titanium oxide coated mica was prepared according to the above-mentioned method, i.e., by using 1 wt % of iron oxide as a photochromic property activating agent and titanium oxide coated mica whose ratio of titanium oxide layer was about 50% and whose interference color was blue and calcinating the mixture at 900° C. Properties of reflectance shown under various light conditions in the obtained titanium oxide coated mica were measured. This result is shown in FIG. 6.

Figure 6:
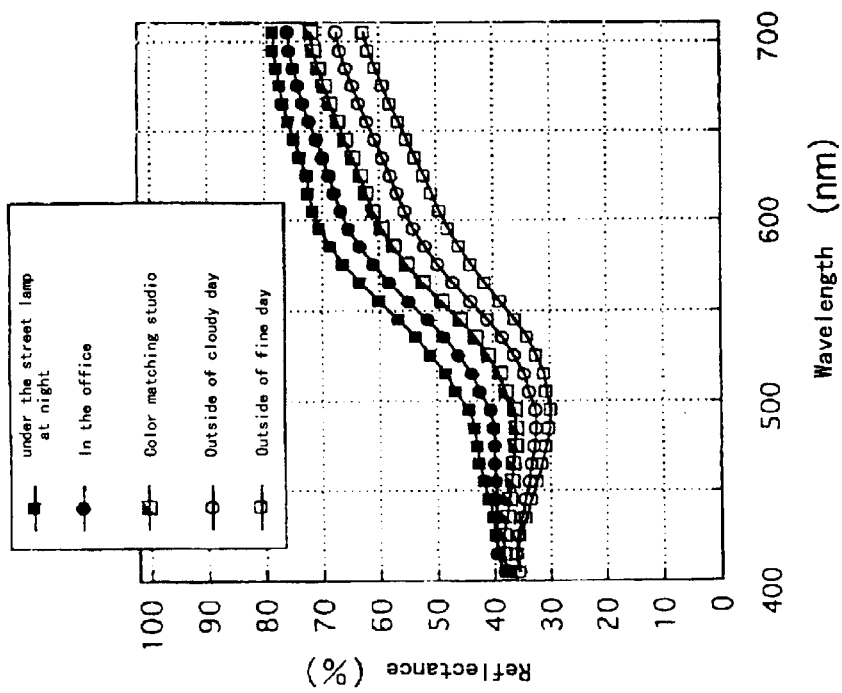
FIG. 6 is a graphic chart showing the relation of the properties of reflectance concerning titanium oxide coated mica in each wavelength.

Judging from the result of FIG. 6, it is found that reflectance around long wave range 500 nm or more of visible light increases under dark environment such as white fluorescent light. On the contrary, it is found that reflectance of long wave range decreases under bright environment such as sunlight. Accordingly, it is possible to obtain a makeup cosmetic preparation having natural and high color-rendering property in response to surrounding light condition by compounding such pigment into the cosmetic preparation.

Study in Amount of Photochromic Titanium Oxide Coated Mica to Cosmetic Preparation A photochromic titanium oxide coated mica was actually compounded into a cosmetic preparation. Then, the properties of the cosmetic preparation were tested. A foundation was manufactured by the titanium oxide coated mica, which was used in test of FIG. 6. The influence on the cosmetic preparation due to the amount of the photochromic titanium oxide coated mica was tested.

The ingredients excluding the photochromic titanium oxide coated mica, which was compounded in the manufactured foundation were shown in TABLE 1. Unit of amount is shown by wt %.

TABLE 1

| Ingredients | Amount |
| --- | --- |
| Talc | 14 |
| Sericite | 24 |
| Kaolin | 10 |
| Globular nylon powder | 2 |
| Globular PMMA powder | 4 |
| Boron nitride powder | 1 |
| Polyehter denatured silicone | 0.5 |
| Sorbitan sesquiisostearate | 1 |
| Liquid paraffin | 3 |
| Dimethylpolysiloxane | 1 |
| Petrolatum | 2 |
| 2-Ethylhexyl 4-methoxycinnamate | 2 |
| Glyceryl triisooctanoate | 0.5 |
| Mica | Balance |
| Antiseptic | Q.S. |
| Fragrance | Q.S. |

To the above-described ingredients was added said photochromic titanium oxide coated mica with changing its amount. The foundation which compounds 0.1 wt %, 3 wt %, 10 wt %, 20 wt %, 30 wt %, and 35 wt % of the photochromic titanium oxide coated mica was defined as Manufacturing Examples 1, 2, 3, 4, 5 and 6, respectively.

The conventional photochromic titanium oxide was compounded with changing its amount in the place of the photochromic titanium oxide coated mica and those effects were also compared. The foundation which compounds 3 wt % and 10 wt % of the conventional titanium oxide was defined a Comparative Examples 1 and 2, respectively.

The foundations of Manufacturing Examples 1 to 6 and Comparative Examples 1 and 2 were tested by 10 persons of professional panel. Items for test were transparency in finish, natural finish, no whiteness in outdoors (weather: fine) and no somberness indoors.

Evaluation was graded according to the criteria as follows.

Very Excellent ◎: 9 or more persons felt very excellent
Excellent ○: 7 to 8 persons felt very excellent
Slightly Excellent Δ: 4 to 6 persons felt very excellent
Almost No Effect X : 3 or less persons felt very well
The result of this functional test is shown in TABLE 2.

TABLE 2

|  | Amount | Transparency | Finish | Outdoor: No Whiteness | Indoor: No Somberness |
|---|---|---|---|---|---|
| Man. Ex. 1 | 0.1 wt % | ◎ | ○ | ◎ | ○ |
| Man. Ex. 2 | 3 wt % | ◎ | ◎ | ◎ | ◎ |
| Man. Ex. 3 | 10 wt % | ◎ | ◎ | ◎ | ◎ |
| Man. Ex. 4 | 20 wt % | ◎ | ○ | ◎ | ◎ |
| Man. Ex. 5 | 30 wt % | ○ | ○ | ○ | ○ |
| Man. Ex. 6 | 35 wt % | ○ | Δ | ○ | ○ |
| Comp. Ex. 1 | 3 wt % | Δ | ○ | ◎ | X |
| Comp. Ex. 2 | 10 wt % | ○ | ○ | ◎ | X |

The result of TABLE 2 shows that the makeup cosmetic preparations of the present invention comprising the photochromic titanium oxide coated mica within the range of 0.1 to 30 wt %, are excellent in every items. In particular, almost all persons answer that the cosmetic preparations comprising the photochromic titanium oxide coated mica within the range of 3 to 10 wt %, are especially excellent.

Judging from these answers, it is observed that the effect for compensating somberness was not obtained sufficiently in the case where the amount of the photochromic titanium oxide coated mica was 3 wt % or less. This was because that manufacturing examples were foundations, however it was found that scattered feeling such as glittering feeling peculiar to pearl ingredient was observed in the cosmetic preparations and it was too much glossy in the case where the amount of photochromic titanium oxide coated mica was more than 10 wt %. Therefore, it is preferable that the amount of the photochromic titanium oxide coated mica for preparing a foundation is 3 to 10 wt %.

On the other hand, the cosmetic preparations comprising the conventional photochromic titanium oxide, were not so bad in evaluation as a whole. However it is difficult to evaluate the cosmetic preparations compatible with surrounding light condition. In particular, there is defective evaluation such as lacks of transparency in finish and somberness indoors.

Study for Compounding with Conventional Photochromic Titanium Oxide

The present inventors tested to obtain the cosmetic preparation, which mixes the photochromic titanium oxide coated mica and the conventional photochromic titanium oxide. The makeup cosmetic preparation of Manufacturing Example 2 in accordance with the present invention, which shows favorable results in the test hereinbefore, was used as the subject for comparison.

To the above-described ingredients, which comprised 3 wt % of the photochromic titanium oxide coated mica in advance were added 1 wt % of the conventional titanium oxide. The makeup cosmetic preparation which compounds 1 wt %, 5 wt %, 10 wt %, 20 wt %, 30 wt %, and 32 wt % of said conventional titanium oxide comprising the photochromic titanium oxide coated mica was defined as Manufacturing Examples 7, 8, 9, 10, 11 and 12, respectively.

Functional test was effected to 10 persons of professional panel. Test method, items for the test and criteria thereof were the same ones as shown in the result of TABLE 2.

The result of this functional test is shown in TABLE 3.

TABLE 3

|  | Amount of PC TiO | Transparency | Finish | Outdoor: No Whiteness | Indoor: No Somberness |
|---|---|---|---|---|---|
| Man. Ex. 2 | 0 wt % | ◎ | ◎ | ○ | ◎ |
| Man. Ex. 7 | 1 wt % | ◎ | ◎ | ◎ | ◎ |
| Man. Ex. 8 | 5 wt % | ◎ | ◎ | ◎ | ◎ |
| Man. Ex. 9 | 10 wt % | ◎ | ◎ | ◎ | ◎ |
| Man. Ex. 10 | 20 wt % | ◎ | ◎ | ◎ | ◎ |
| Man. Ex. 11 | 30 wt % | ○ | ○ | ◎ | ◎ |
| Man. Ex. 12 | 32 wt % | Δ | Δ | ◎ | ◎ |

As a result of TABLE 3, the makeup cosmetic preparation that the photochromic titanium oxide coated mica and the conventional photochromic titanium oxide were mixed, receives higher evaluation than the cosmetic preparation comprising only the photochromic titanium oxide coated mica. In Manufacturing Example 2, which obtained favorable evaluation in the test hereinbefore, the answers that the cosmetic preparation was felt whiteness outdoors, were particularly increased as compared with the cosmetic preparation, which further comprised conventional photochromic titanium oxide.

The result also shows that the makeup cosmetic preparations of the present invention which compound 1 to 30 wt % of the conventional photochromic titanium oxide were excellent in every items in the case where the photochromic titanium oxide coated mica was mixed with the conventional photochromic titanium oxide. In particular, almost all persons answered that the cosmetic preparations, which compound 1 to 20 wt % of the conventional photochromic titanium oxide, were very excellent.

However, some panels answered that the cosmetic preparation, which compound 1 wt % of the conventional photochromic titanium oxide was short of hiding ability. On the contrary, many persons answered that transparency was lost and its finish was unnatural due to high hiding ability in the case where 30 wt % or more of the conventional photochromic titanium oxide was compounded. Accordingly, it is preferable that 1 to 30 wt %, and more particularly, 5 to 20 wt % of the conventional photochromic titanium oxide is compounded in the cosmetic preparation of the present invention together with the photochromic titanium oxide coated mica.

Judging from the studies mentioned hereinbefore, it is found that the foundation, one of the light-responding high color-rendering makeup cosmetic preparation of the present invention shows natural color-rendering in response to surrounding light condition according as follows. Namely, a photochromic titanium oxide coated mica pigment is manufactured by adding 0.3 to 2.0 wt % of iron oxide to titanium oxide coated mica whose ratio of titanium oxide layer is 47 to 57 under 850 to 950° C. of calcination temperature. A cosmetic preparation comprises 0.1 to 30 wt % and, more particular, 3 to 10 wt % of said pigment, and further comprises 1 to 30 wt % and, more particular, 5 to 20 wt % of the conventional photochromic titanium oxide.

Next, preparation examples of the makeup cosmetic preparation will be described. Unit of amount is shown by wt %.

PREPARATION EXAMPLE 1

Powdery Foundation

| | | |
|---|---|---|
| 1. | Photochromic titanium oxide coated mica | 10 |
| 2. | Conventional photochromic titanium oxide | 8 |
| 3. | Talc | 15 |
| 4. | Sericite | 25 |
| 5. | Iron oxide | 5 |
| 6. | Spherical nylon powder | 2 |
| 7. | Spherical PMMA powder | 4 |
| 8. | Boron nitride powder | 1 |
| 9. | Mica | Balance |
| 10. | Polyether modified silicone | 0.5 |
| 11. | Sorbitan sesquiisostearate | 1 |
| 12. | Liquid paraffin | 3 |
| 13. | Dimethylpolysiloxane | 1 |
| 14. | Petrolatum | 2 |
| 15. | 2-Ethylhexyl 4-methoxycinnamate | 2 |
| 16. | Glyceryl triisooctanoate | 0.5 |
| 17. | Antiseptic | Q.S. |
| 18. | Fragrance | Q.S. |

The ingredients 1 to 9 were mixed in uniform. The ingredients 10 to 18 heated and dissolved in advance were added thereto and the mixture was mixed again in uniform. A powdery foundation was obtained by filling the mixture into a container. The reflectance of this powdery foundation in each wavelength range of reflected light was measured by changing light condition. This result is shown in FIG. 7.

Figure 7:
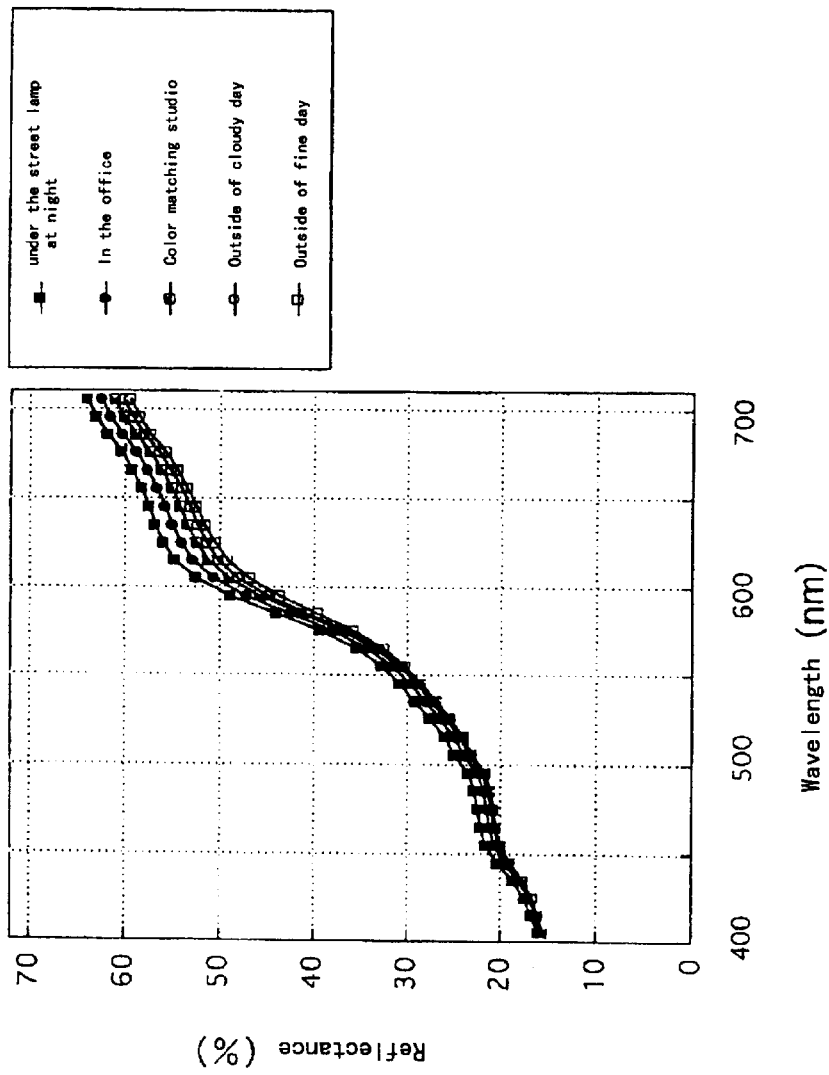
FIG. 7 is a graphic chart showing the relation of reflectance in each wavelength in the reflected light of the powdery foundation of the present invention.

As is clear from FIG. 7, the powdery foundation shown in Preparation Example 1 has reflectance distribution of each wavelength range near to bare skin. Reflectance of long wavelength range decreases in a light place while it increases in a dark place. The powdery foundation shown in Preparation Example 1 rendered the color close to bare skin in response to surrounding light condition.

PREPARATION EXAMPLE 2

Oil based Foundation

| | | |
|---|---|---|
| 1. | Photochromic titanium oxide coated mica | 10 |
| 2. | Conventional photochromic titanium oxide | 10 |
| 3. | Zinc oxide | 8 |
| 4. | Iron oxide (red) | 2 |
| 5. | Iron oxide (yellow) | 4.7 |
| 6. | Iron oxide (black) | 0.3 |
| 7. | Solid pareffin | 10 |
| 8. | Petrolatum | 15 |
| 9. | Almond oil | 7 |
| 10. | Liqid paraffin | 30 |
| 11. | Solbitan sesqui oleic acid ester | 3 |
| 12. | Fragrance | Q.S. |
| 13. | Antiseptic, Antioxidant | Q.S. |

The ingredients 3 to 6 were mixed and pulverized. The ingredients 1 and 2 were added thereto and both were mixed more uniform. The ingredients a part of 10 and 11 were added thereto and both were mixed in uniform.(obtain the powder part) The ingredients the rest of 10, 7 to 9,12 and 13 were mixed by heated and dissolved. The powder part were added thereto and both were cooled down to 40° C. with dispersing well. An oil based foundation was obtained by filling the mixture into a container. The oil based foundation obtained by Preparation Example 2 also rendered the color close to bare skin in response to surrounding light condition.

PREPARATION EXAMPLE 3

Oil-in-Water Emulsion Foundation

| | | |
|---|---|---|
| 1. | Photochromic titanium oxide coated mica | 5 |
| 2. | 1,3-Butylene glycol | 7 |
| 3. | Glycerine | 3 |
| 4. | Bentonite | 1 |
| 5. | Potassium hydroxide | 0.2 |
| 6. | Triethanolamine | 9 |
| 7. | Purified water | Balance |
| 8. | Titanium dioxide | 9 |
| 9. | Iron oxide | 4 |
| 10. | Spherical silica powder | 7 |
| 11. | Dimethylpolysiloxane | 10 |
| 12. | Liquid paraffin | 8 |
| 13. | Glyceryl monostearate | 1 |
| 14. | Polyoxyethylene sorbitan monostearate | 0.8 |
| 15. | Cetyl alcohol | 1 |
| 16. | Antiseptic | Q.S. |
| 17. | Fragrance | Q.S. |

The ingredients 2 to 7 were dissolved in uniform. The ingredients 1 to 10 were mixed, pulverized in advance, and dispersed. The ingredients 11 to 17 heated and dissolved were added thereto to obtain an oil-in-water emulsion foundation by filling the mixture into a container. The foundation obtained by Preparation Example 3 also rendered the color close to bare skin in response to surrounding light condition.

PREPARATION EXAMPLE 4

Water-in-Oil Emulsion Foundation

| | | |
|---|---|---|
| 1. | Photochromic titanium oxide coated mica | 10 |
| 2. | Spherical nylon powder | 2 |
| 3. | Titanium dioxide processed with silicone | 10 |
| 4. | Iron oxide processed with silicone | 5 |
| 5. | Sericite processed with silicone | 1 |
| 6. | Mica processed with silicone | 1.5 |
| 7. | Talc processed with metallic soap | 5.5 |
| 8. | Purified water | Balance |
| 9. | Sodium hydroxymethoxybenzophenone sulfonate | 3 |
| 10. | Glycerine | 10 |
| 11. | Dipropylene glycol | 5 |
| 12. | Decamethylcyclopentasiloxane | 10 |
| 13. | Liquid paraffin | 3 |
| 14. | Methylphenyl polysiloxane | 1 |
| 15. | Silicone resin | 5 |
| 16. | Sorbitan monoisostearate | 2 |
| 17. | Polyoxyethylene modified silicone | 0.5 |
| 18. | Antiseptic | Q.S. |
| 19. | Fragrance | Q.S. |

The ingredients 12 to 19 were mixed and dissolved in uniform. The ingredients 1 to 7 were mixed, pulverized in advance, and dispersed. The ingredients 8 to 11 mixed and stirred were added thereto and emulsified to obtain a water-in-oil emulsion foundation filling the mixture into a container. The foundation obtained by Preparation Example 4 also rendered the color close to bare skin in response to surrounding light condition.

PREPARATION EXAMPLE 5

Water-in-Oil Emulsion Foundation

| | | |
|---|---|---|
| 1. | Photochromic titanium oxide coated mica | 10 |
| 2. | Globular nylon powder | 2 |
| 3. | Conventional photochromic titanium oxide processed with silicone | 10 |
| 4. | Iron oxide processed with silicone | 5 |
| 5. | Sericite processed with silicone | 1 |
| 6. | Mica processed with silicone | 1.5 |
| 7. | Talc processed with metallic soap | 5.5 |
| 8. | Purified water | Balance |
| 9. | Sodium hydroxymethoxybenzophenone sulfonate | 3 |
| 10. | Glycerine | 10 |
| 11. | Dipropylene glycol | 5 |
| 12. | Decamethylcyclopentasiloxane | 10 |
| 13. | Liquid paraffin | 3 |
| 14. | Methylphenyl polysiloxane | 1 |
| 15. | Silicone resin | 5 |
| 16. | Sorbitan monoisostearate | 2 |
| 17. | Polyoxyethylene modified silicone | 0.5 |
| 18. | Antiseptic | Q.S. |
| 19. | Fragrance | Q.S. |

The ingredients 12 to 19 were mixed and dissolved in uniform. The ingredients 1 to 7 were mixed, pulverized in advance, and dispersed. The ingredients 8 to 11 mixed and stirred were added thereto and emulsified to obtain a water-in-oil emulsion foundation filling the mixture into a container. The foundation obtained by Preparation Example 5 also rendered the color close to bare skin in response to surrounding light condition.

PREPARATION EXAMPLE 6

Face Powder

| | | |
|---|---|---|
| 1. | Photochromic titanium oxide coated mica | 15 |
| 2. | Sericite | 10 |
| 3. | Globular powder of organopolysiloxane elastomer | 5 |
| 4. | Boron nitride | 20 |
| 5. | Iron oxide | 3 |
| 6. | Magnesium carbonate | 3 |
| 7. | Talc | Balance |
| 8. | Spherical aluminum powder | 4 |
| 9. | Squalane | 2 |
| 10. | Glyceryl trioctanoate | 3 |
| 11. | Sorbitan sesquioleate | 1 |
| 12. | Antiseptic | Q.S. |
| 13. | Fragrance | Q.S. |

The ingredients 1 to 8 were mixed and pulverized. The ingredients 9 to 13 were mixed in advance were added thereto and both were mixed and stirred. A face powder was obtained by filling the mixture into a container. The face powder obtained by Preparation Example 6 rendered the color in response to surrounding light condition, i.e., bright in a dark place and inhibiting whiteness properly in a light place.

PREPARATION EXAMPLE 7

Face Powder

| | | |
|---|---|---|
| 1. | Photochromic titanium oxide coated mica | 15 |
| 2. | Sericite | 10 |
| 3. | Globular powder of organopolysiloxane elastomer | 5 |
| 4. | Boron nitride | 20 |
| 5. | Iron oxide | 3 |
| 6. | Magnesium carbonate | 3 |
| 7. | Conventional photochromic titanium oxide | 1 |
| 8. | Talc | Balance |
| 9. | Globular aluminum powder | 4 |
| 10. | Squalane | 2 |
| 11. | Glyceryl trioctanoate | 3 |
| 12. | Sorbitan sesquioleate | 1 |
| 13. | Antiseptic | Q.S. |
| 14. | Fragrance | Q.S. |

The ingredients 1 to 9 were mixed and pulverized. The ingredients 10 to 14 mixed in advance were added thereto and both were mixed and stirred. A face powder was obtained by filling the mixture into a container. The face powder obtained by Preparation Example 7 rendered the color in response to surrounding light condition, i.e., bright in a dark place and inhibiting whiteness properly in a light place.

PREPARATION EXAMPLE 8

Eye Shadow

| | | |
|---|---|---|
| 1. | Photochromic titanium oxide coated mica | 7 |
| 2. | Sericite | 7 |
| 3. | Mica | 15 |
| 4. | Boron nitride | 33 |
| 5. | Titanium oxide coated mica | 2 |
| 6. | Iron oxide | 1.5 |
| 7. | Talc | Balance |
| 8. | Squalane | 2 |
| 9. | Dimethylpolysiloxane | 2 |
| 10. | Silicone resin | 1.5 |
| 11. | Sorbitan monooleate | 0.5 |
| 12. | Antiseptic | Q.S. |
| 13. | Fragrance | Q.S. |

The ingredients 1 to 7 were mixed and pulverized. The ingredients 8 to 13 mixed in advance were added thereto and both were mixed and pulverized. An eye shadow was obtained by molding the mixture into a medium-sized plate. The eye shadow obtained by Preparation Example 8 rendered the color in response to surrounding light condition, i.e., bright color tone with red in a dark place and inhibiting lightness of color tone properly in a light place.

PREPARATION EXAMPLE 9

Eye Shadow

| | | |
|---|---|---|
| 1. | Photochromic titanium oxide coated mica | 7 |
| 2. | Sericite | 7 |
| 3. | Mica | 15 |
| 4. | Boron nitride | 33 |
| 5. | Titanium oxide coated mica | 2 |
| 6. | Iron oxide | 1.5 |

-continued

|    |                                     |         |
|----|-------------------------------------|---------|
| 7. | Conventional photochromic titanium oxide | 3       |
| 8. | Talc                                | Balance |
| 9. | Squalane                            | 2       |
| 10.| Dimethylpolysiloxane                | 2       |
| 11.| Silicone resin                      | 1.5     |
| 12.| Sorbitan monooleate                 | 0.5     |
| 13.| Antiseptic                          | Q.S.    |
| 14.| Fragrance                           | Q.S.    |

The ingredients 1 to 8 were mixed and pulverized. The ingredients 9 to 14 mixed in advance were added thereto and both were mixed and pulverized. An eye shadow was obtained by molding the mixture into a medium-sized plate. The eye shadow obtained by Preparation Example 9 rendered the color in response to surrounding light condition, i.e. bright color tone with red in a dark place and inhibiting lightness of color tone properly in a light place.

PREPARATION EXAMPLE 10

Lipstick

|     |                                                     |         |
|-----|-----------------------------------------------------|---------|
| 1.  | Photochromic titanium oxide coated mica             | 10      |
| 2.  | Carnauba wax                                        | 1       |
| 3.  | Candelilla wax                                      | 2       |
| 4.  | Ceresine                                            | 10      |
| 5.  | Glyceryl triisooctanoate                            | 9       |
| 6.  | Glyceryl diisostearate                              | 13      |
| 7.  | Dimethylpolysiloxane (vis.: 90,000 mPa.s at 25° C.) | 5       |
| 8.  | Dimethylpolysiloxane (vis.: 10 mPa.s at 25° C.)     | 5       |
| 9.  | Silicone resin                                      | 8       |
| 10. | Squalane                                            | Balance |
| 11. | Hydroxypropyl-β-cyclodextrin                        | 1       |
| 12. | Cholesteryl macadamia nut fatty acid oil            | 3.5     |
| 13. | Synthetic sodium magnesium silicate                 | 0.5     |
| 14. | Hydrophobic silica                                  | 0.5     |
| 15. | Purified water                                      | 2       |
| 16. | Coloring material                                   | Q.S.    |
| 17. | Antiseptic                                          | Q.S.    |
| 18. | Fragrance                                           | Q.S.    |

The ingredients 13 and 14 were dispersed into the ingredient 12 heated up to 60° C. The ingredients 11 and 15 dissolved in uniform were added thereto and it was stirred sufficiently. The mixture was added to the ingredients 2 to 10 heated and dissolved separately with the foregoing ingredients and it was further stirred sufficiently. The ingredients 1 and 16 to 18 were added thereto and the mixture was stirred and dispersed. Then, a lipstick was obtained by filling the dispersion into a container. The lipstick obtained by Preparation Example 10 rendered the color in response to surrounding light condition, i.e., bright color tone with red in a dark place and inhibiting lightness of color tone properly in a light place.

Though we have explained by using the photochromic titanium oxide coated mica whose object color is reddish orange and whose interference color is blue, which is prepared by adding 0.3 to 2.0 wt % of iron oxide as a photochromic property activating agent to titanium oxide coated mica whose ratio of titanium oxide layer is 47 to 57% and calcinating at 850 to 950° C., the present invention is not restricted to the makeup cosmetic preparation which comprises only this photochromic titanium oxide coated mica.

For example, in order to color a cosmetic preparation with purple, the photochromic titanium oxide coated mica which renders purple object color and yellow interference color having high photochromic property, is made by adding cobalt as a photochromic property activating agent to a titanium oxide coated mica whose ratio of titanium oxide layer is about 42%. Also, in order to color a cosmetic preparation with red, the photochromic titanium oxide coated mica which renders red object color and green interference color having high photochromic property is made by adding copper as a photochromic property activating agent to a titanium oxide coated mica whose ratio of titanium oxide layer is about 55%.

As like the examples mentioned hereinbefore, the observation color changeable type photochromic titanium oxide coated mica rendering the objective color tone can be obtained by using with selection of the photochromic property activating agent, which renders the color tone to be colored as the object color of titanium oxide coated mica and by adjusting layer thickness of titanium oxide layer in the titanium oxide coated mica properly, in order that the interference color may renders different color tone with the object color. Also, a makeup cosmetic preparation which exhibits high color-rendering property in response to surrounding light can be made by adding such titanium oxide coated mica.

As mentioned hereinbefore, the most suitable change of color tone adopted to any light conditions such as indoor and outdoor can be actualized without spoiling natural and transparent finish according to the light-responding color-rendering makeup cosmetic preparation of the present invention.

What is claimed is:

1. A light-responding-and-high-color-rendering-makeup-cosmetic preparation comprising an observation-color-changeable-photochromic-titanium-oxide-coated mica wherein:

(a) said observation-color-changeable-photochromic-titanium-oxide mica reversibly changes its color tone in response to irradiation by ultraviolet light; said color tone being visually observed as an observation color;

(b) said observation-color-changeable-photochromic-titanium-oxide mica comprises:

(i) mica;

(ii) a layer of either titanium oxide or titanium-oxide compound coated on the surface of said mica and each having photochromic property of darkening said layer in response to changing intensity of said ultraviolet light; and (iii) metal or metal compound deposed on the surface and/or inside of said layer and whose color is observed as an object color; and (c) at least one color tone of said preparation is given by said observation color of said observation-color-changeable-photochromic-titanium-oxide mica.

2. A light-responding-and-high-color-rendering-makeup-cosmetic preparation according to claim 1, wherein the thickness of said titanium oxide layer in said observation-color-changeable-photochromic-titanium-oxide-coated is so adjusted that the color tone of the interference color generated by said titanium oxide layer shows a color different from the object color.

3. A light-responding-and-high-color-rendering-makeup-cosmetic preparation according to claim 2, wherein said thickness of said titanium oxide layer is so adjusted that said color tone shows a complementary color or a color gamut which is in the vicinity of the complementary color of the object color.

4. A light-responding-and-high-color-rendering-makeup-cosmetic preparation according to claim 1, wherein said observation-color-changeable-photochromic-titanium-oxide-coated mica is a photochromic titanium oxide coated mica whose reflectance of the light around long wavelength range of visible light decreases in a light place and increases in a dark place.

5. A light-responding-and-high-color-rendering-makeup-cosmetic preparation according to claim 3, wherein said observation-color-changeable-photochromic-titanium-oxide-coated mica comprises either iron oxide or a compound which is mainly composed of iron oxide.

6. A light-responding-and-high-color-rendering-makeup-cosmetic preparation according to claim 3, wherein the amount of either said titanium oxide or said titanium-oxide compound is from about 47 to about 57% wt.

7. A light-responding-and-high-color-rendering-makeup-cosmetic preparation according to claim 3, wherein said observation-color-changeable-photochromic-titanium-oxide-coated mica is calcinated at 850 to 950° C.

8. A light-responding-and-high-color-rendering-makeup-cosmetic preparation according to claim 1, wherein the amount of said observation-color-changeable-photochromic-titanium-oxide-coated mica is from about 0.1 to about 30 wt %.

9. A light-responding-and-high-color-rendering-makeup-cosmetic preparation according to claim 1, wherein 1 to 30 wt % of a photochromic titanium oxide which mainly changes its lightness in response to an exposure to light is compounded together with said observation-color-changeable-photochromic-titanium-oxide-coated mica.

* * * * *